(12) United States Patent
Bousamra (10) Patent No.: US 11,864,888 B2
(45) Date of Patent: Jan. 9, 2024

(54) USER-DEFINED STRUCTURED TESTING FOR USE IN DIABETES CARE

(71) Applicant: Roche Diabetes Care, Inc., Indianapolis, IN (US)

(72) Inventor: Steven A. Bousamra, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 884 days.

(21) Appl. No.: 16/570,664

(22) Filed: Sep. 13, 2019

(65) Prior Publication Data

US 2020/0000385 A1   Jan. 2, 2020

Related U.S. Application Data

(62) Division of application No. 13/107,301, filed on May 13, 2011, now Pat. No. 10,448,869.

(51) Int. Cl.
| | | |
|---|---|---|
| *A61B 5/145* | (2006.01) | |
| *G16H 10/20* | (2018.01) | |
| *G16H 30/20* | (2018.01) | |
| *G16H 10/40* | (2018.01) | |

(52) U.S. Cl.
CPC ......... *A61B 5/14532* (2013.01); *G16H 10/20* (2018.01); *G16H 10/40* (2018.01); *G16H 30/20* (2018.01)

(58) Field of Classification Search
CPC .. A61B 5/0002; A61B 5/14532; G16H 15/00; G16H 20/10; G16H 10/20; G16H 20/17
See application file for complete search history.

(56) References Cited

U.S. PATENT DOCUMENTS

| | | |
|---|---|---|
| 4,803,625 A | 2/1989 | Fu et al. |
| 2002/0019747 A1 | 2/2002 | Ware et al. |
| 2004/0242973 A1 | 12/2004 | Tanabe et al. |
| 2005/0215868 A1* | 9/2005 | Kenjou .............. A61B 5/14532 600/300 |
| 2006/0010098 A1 | 1/2006 | Goodnow et al. |

(Continued)

FOREIGN PATENT DOCUMENTS

| | | |
|---|---|---|
| CN | 1477941 A | 2/2004 |
| CN | 101308528 A | 11/2008 |
| WO | WO-2010/089304 A1 | 8/2010 |

*Primary Examiner* — Matthew Kremer
*Assistant Examiner* — Kyle W. Kretzer
(74) *Attorney, Agent, or Firm* — Harness, Dickey & Pierce, P.L.C.

(57) ABSTRACT

A method is provided for constructing a structured test having user-defined adherence criteria. The method includes: presenting a patient with a plurality of contextual criterion for a structured test; receiving selection of one or more contextual criterion from the plurality of contextual criterion; and constructing a structured test that includes the contextual criterion selected by the patient. During administration of the structured test, each of the contextual criteria selected by the patient is evaluated. Sample data acquired during the structured test is reported as compliant when each of the context criterion selected by the patient was met during the administration of the structured test or tagged as non-compliant when at least one contextual criterion was not met during the administration of the structured test.

18 Claims, 7 Drawing Sheets

(56) References Cited

U.S. PATENT DOCUMENTS

| | | | |
|---|---|---|---|
| 2007/0213604 A1* | 9/2007 | Brown | A61B 5/14532 600/300 |
| 2008/0071580 A1* | 3/2008 | Marcus | G16H 40/67 705/3 |
| 2008/0177149 A1 | 7/2008 | Weinert et al. | |
| 2009/0247931 A1* | 10/2009 | Damgaard-Sorensen | G06F 1/1656 715/764 |
| 2010/0016700 A1 | 1/2010 | Sieh et al. | |
| 2010/0160740 A1* | 6/2010 | Cohen | A61B 5/4833 600/300 |
| 2010/0160757 A1 | 6/2010 | Weinert et al. | |
| 2010/0198142 A1 | 8/2010 | Sloan et al. | |
| 2010/0212675 A1 | 8/2010 | Walling et al. | |
| 2010/0218132 A1 | 8/2010 | Soni et al. | |
| 2011/0082709 A1* | 4/2011 | Li | G16H 20/60 707/769 |

\* cited by examiner

USER-DEFINED STRUCTURED TESTING FOR USE IN DIABETES CARE

This application is a divisional of U.S. patent application Ser. No. 13/107,01, filed May 13, 2011. The entire disclosure of the above application is incorporated herein by reference.

FIELD

The present disclosure relates to structured testing methods for diagnostics and therapy support of patients with chronic disease, such as diabetes.

BACKGROUND

For people with diabetes, successful management requires monitoring the effects lifestyle changes can have in both short-term and long-term time frames. Regular testing of their blood glucose level can be an important part of diabetes management as a way to track changes throughout the day. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood allowing it to measure the concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor glucose levels in one's home, healthcare facility or other location, for example, by persons having diabetes or by a healthcare professional.

Patients and healthcare professionals may thereby track and analyze glucose measurements over a period of time to assess changes in the patient over the course of a day, week or other desirable timeframe. For example, some healthcare professionals may instruct a patient to obtain glucose measurements seven or more times a day over a course of a few consecutive days so that patients may observe the changes their measurements undertake. However, the significance in changing lifestyle factors, such as meal portions or physical activity) may not understood by the patients. Thus, it may be desirable to provide methods and devices that enable patients better understand which factors may impact glucose measurements. This section provides background information related to the present disclosure which is not necessarily prior art.

SUMMARY

In one aspect the present disclosure, a method is provided for measuring glucose levels that enable patients to better understand which factors may impact the blood glucose measure. The method includes: receiving from the patient an objective for a structured test; selecting a test template that corresponds to the objective from a plurality of predefined test templates; presenting the patient with a plurality of contextual criterion associated with the selected test template; receiving selection of one or more contextual criterion from the plurality of contextual criterion; constructing a structured test that includes the selected contextual criterion; and administering the structured test to the patient, where the structured test includes prompting the patient to input a sample of blood into a glucose meter.

In another aspect of the disclosure, a method is provided for constructing a structured test having user-defined adherence criteria. The method includes: presenting a patient with a plurality of contextual criterion for a structured test; receiving selection of one or more contextual criterion from the plurality of contextual criterion; and constructing a structured test that includes the contextual criterion selected by the patient. During administration of the structured test, each of the contextual criteria selected by the patient is evaluated. Sample data acquired during the structured test is reported as compliant when each of the context criterion selected by the patient was met during the administration of the structured test or tagged as non-compliant when at least one contextual criterion was not met during the administration of the structured test.

In yet another aspect of the disclosure, the method for constructing a structured test is extended to testing in pairs type tests. The method includes: prompting the patient to input a sample of blood into a glucose meter before and after a given event within a window of time that encapsulates the given event; determining a blood glucose measure from the sample of blood input to the glucose meter; presenting a query to the patient for contextual data regarding another event that occurs outside the window of time; receiving a reply to the query from the patient; and associating the reply with the blood glucose measure.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

Figure 1:
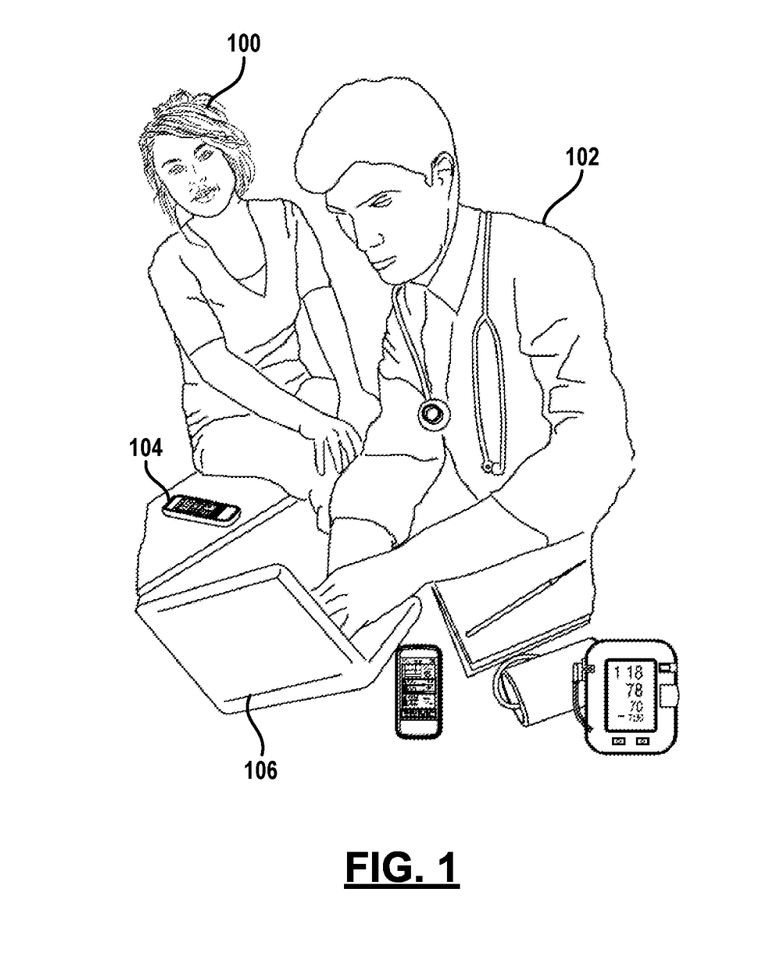
FIG. 1 is a drawing depicting a patient and a treating clinician.

Referring to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician. While this disclosure makes reference to diabetes care, it is readily understood that the concepts related to structured testing disclosed herein can be applied to other types of chronic diseases. Likewise, this disclosure makes reference to blood glucose measures but the concepts are extendable to other types of biomarker of a patient including but not limited to an interstitial glucose value, an HbA1c value, a heart rate measurement, a blood pressure measurement, lipids, triglycerides, cholesterol and the like.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
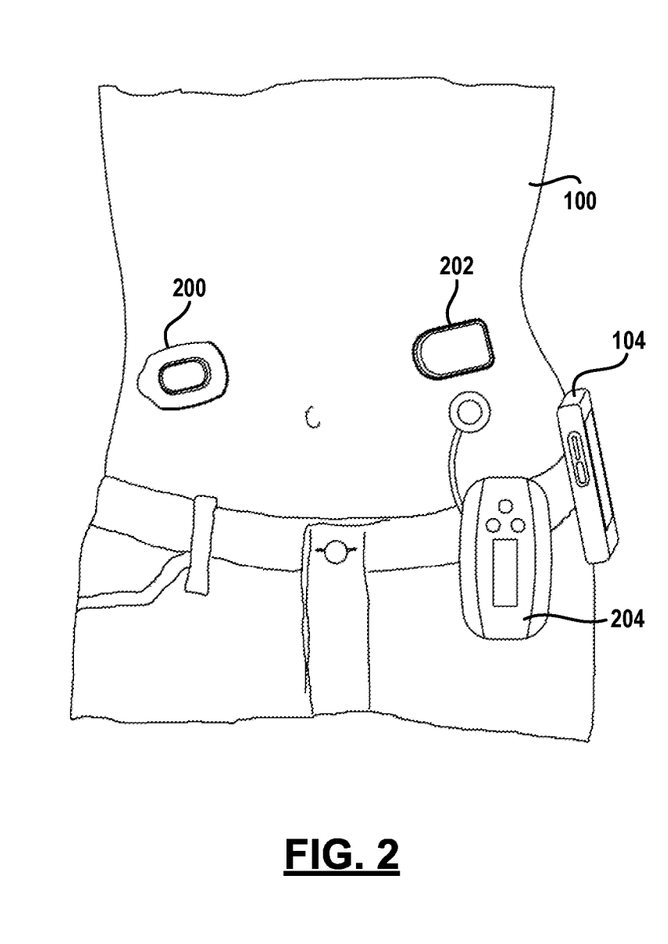
FIG. 2 is a drawing illustrating a patient with a continuous glucose monitor (CGM), an ambulatory durable insulin infusion pump, an ambulatory non-durable insulin infusion pump, and a diabetes manger.

Referring to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in a scheduled manner in the form of a basal dose, which maintains a predetermined insulin level in the blood of the patient 100. Additionally, insulin can be delivered in the form of a bolus dose, which raises the amount of insulin in the blood of the patient 100 by a predetermined amount.

Figure 3:
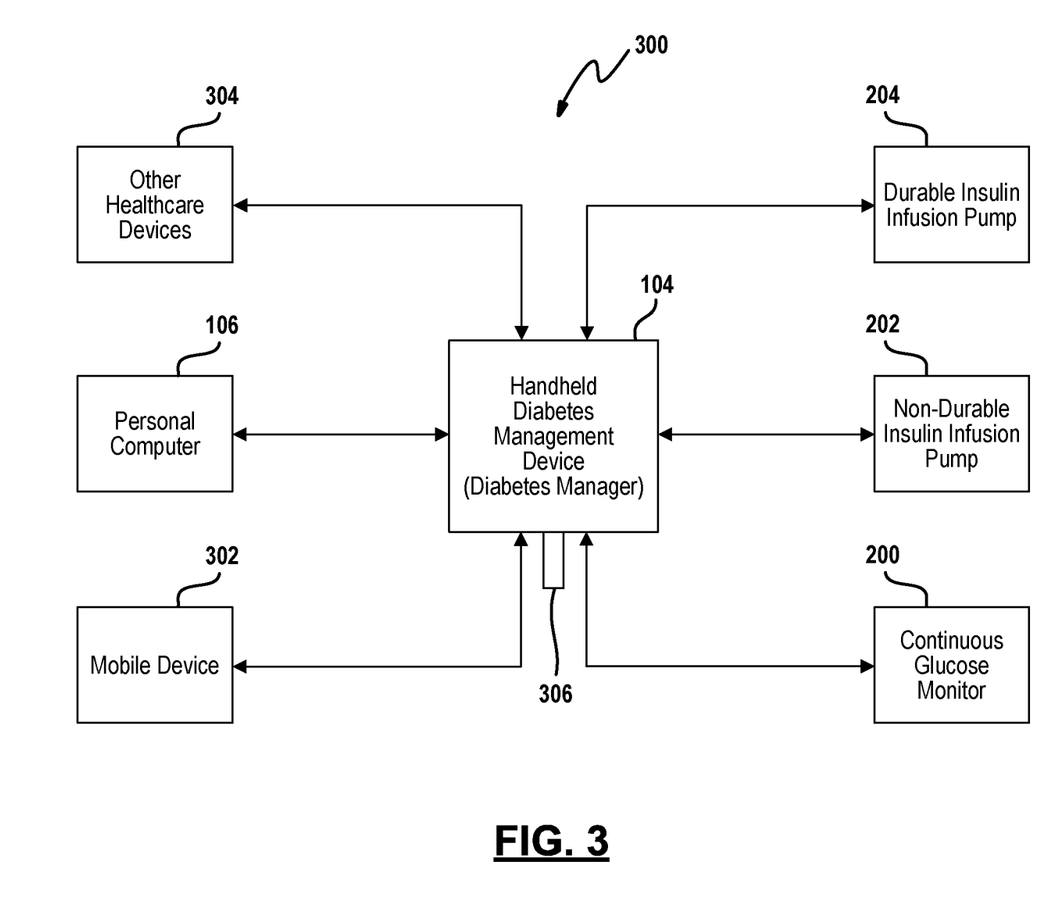
FIG. 3 is a diagram showing an exemplary diabetes management system used by patients and clinicians to manage diabetes.

Referring to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the insulin pump 204 or the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly, for example, using a proprietary Gazell wireless protocol developed by Nordic Semiconductor, Inc.

Additionally, the diabetes manager 104 includes a blood glucose meter (BGM) and a port that communicates with the BGM (not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100. To create repeatable objective evidence that can be used to make a medical assessment or optimization, diabetes manager 104 may execute one or more structured tests or collection procedures as further described below.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can recommend an amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wired communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications. Accu-Chek 360® Diabetes Management System is an example of a commercially available diabetes management software product although other products also fall within the scope of this disclosure.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 4:
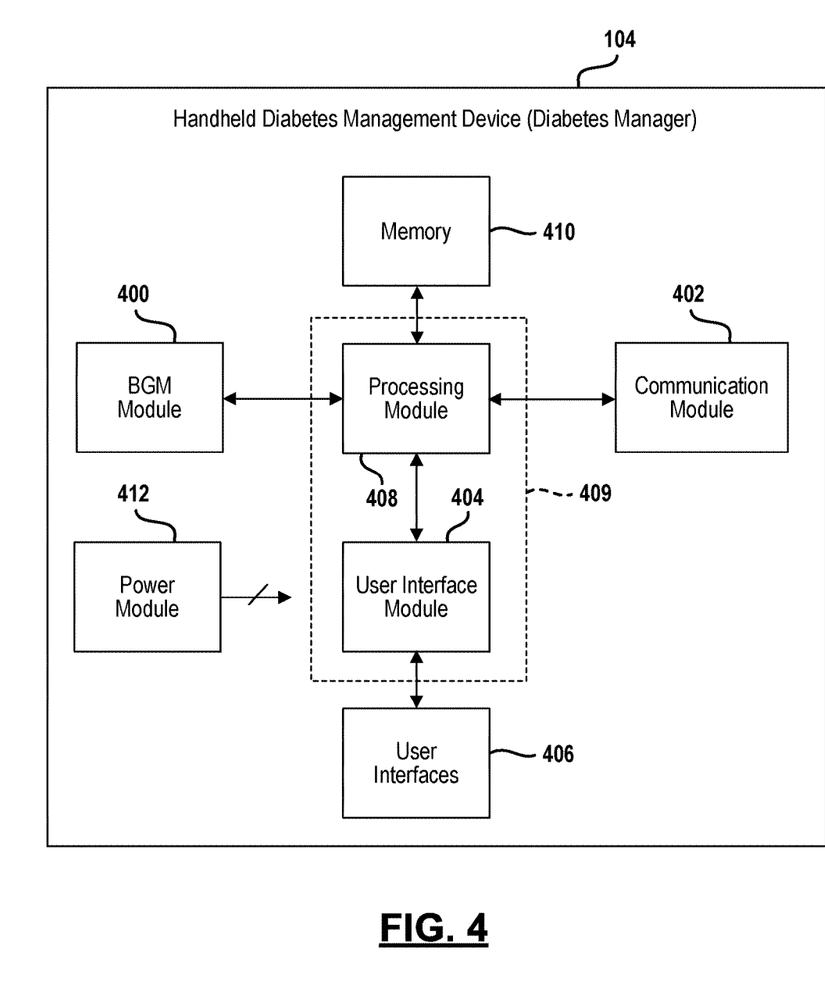
FIG. 4 is a functional block diagram of an exemplary diabetes manager.

An exemplary diabetes manager 104 is further described in relation to FIG. 4. The diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

For purposes of this disclosure, the diabetes manager 104 serves as a collection device. However, the collection device can be any portable electronic device that can provide an acquisition mechanism for determining and storing physiological measures of a person. For example, self-monitoring blood glucose meters and continuous glucose monitor devices are examples of collection devices used for measuring blood glucose in diabetes care. In these examples, the diabetes manager (which may, for example, reside is a portable phone) works cooperatively with a physically separated collection device to administer a structured test and record data associated with the administered test. That is, the diabetes manager may prompt a person to input a sample of blood into a glucose meter or otherwise interact with the person in accordance with the structured test; whereas, the glucose meter analyzes blood samples and stores glucose measures from the blood samples. Glucose measures may be subsequently transmitted to the diabetes manager for further processing.

Figure 5A:
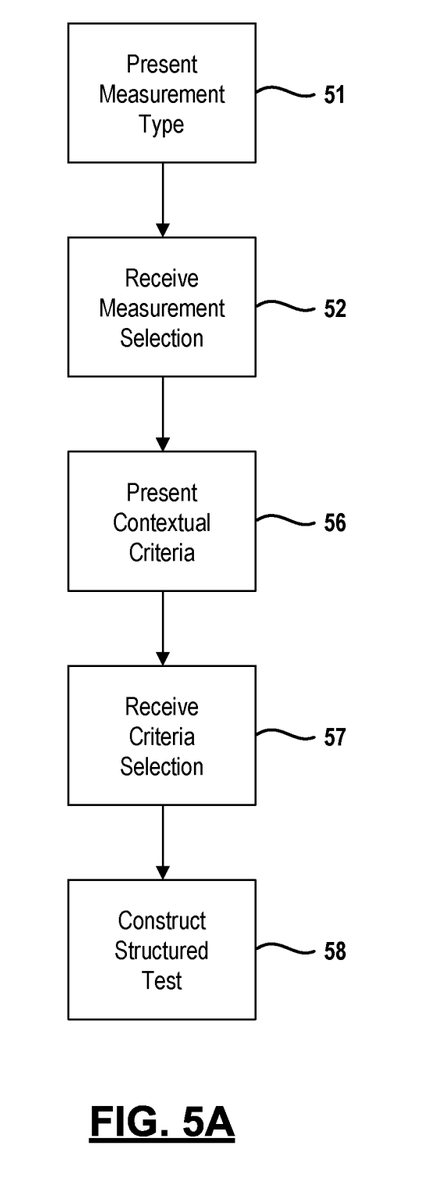
FIGS. 5A and 5B are flowcharts illustrating exemplary methods by which patients are able to construct structured tests.
Figure 5B:
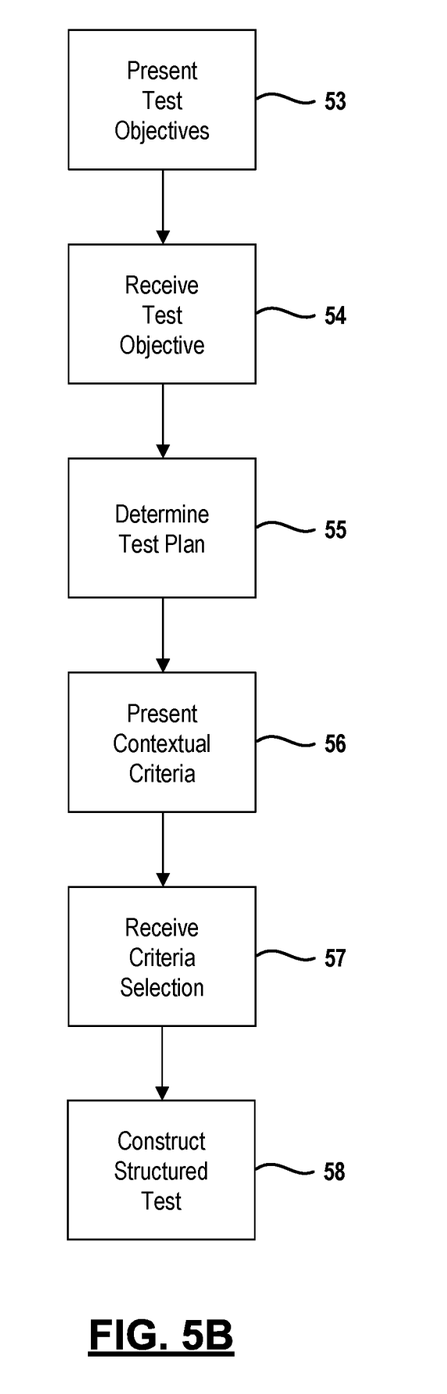

FIGS. 5A and 5B depict exemplary methods by which patients are able to construct a structured test that enables patients to better understand factors which may impact blood glucose measurements. In an exemplary embodiment, the methods for constructing and administering structured tests are implemented in software executed by a processor of the diabetes manager 104. It is envisioned that a structured test could be constructed by a patient (or physician) on another device (e.g., a desktop PC) and subsequently downloaded for execution by the diabetes manager 104.

With reference to FIG. 5A, a patient may begin by selecting a particular type of blood glucose measure that is of interest to the patient. For example, the patient may be interested in what factors impact a fasting blood glucose measure, a pre-prandial glucose measure, or a postprandial glucose measure. In another example, patients may be interested in factors that impact a series of paired glucose tests to help understand particular issues with behavior or therapy. Each paired glucose test involves obtaining pairs of bG measurements before and after particular events. For example, an individual can obtain a bG value before a specific meal, for example before lunch, and another bG value within a specified time after lunch. The "before" and "after" bG values form a related "pair" of bG values and is commonly referred to as a "Testing In Pairs" (TIPs) test. Other types of measurements are also contemplated by this disclosure.

In an exemplary embodiment, a plurality of different measurement types are stored in the diabetes manager and presented at 51 on a display for selection by the patient. The patient in turn selects a particular type of measurement which is captured at 52 by the diabetes manager. For example, the patient may select a morning fasting measure. For this type of measurement, the patient abstains from eating or drinking for a period of time prior to obtaining a blood glucose measure. The patient, however, may not understand what factors effect the measurement. Thus, the patient is presented at 56 with a proposed test template for this particular type of measurement.

Each type of measurement maps to a proposed test template. In operation, the diabetes manager retrieves the proposed test template that corresponds to the measurement selection. The proposed test template is comprised of a series of events to be performed by the patient, including a prompt for the patient to provide a sample of blood to a glucose meter. The proposed test template will further include contextual criteria which may affect the measurement. The proposed test template for a morning fasting measure may include the following events:

Test template for morning fast:
Prompt patient to take a baseline bG measure prior to snack
Prompt patient for information about the snack
Prompt patient to take evening insulin
Confirm amount of insulin taken by the patient
Prompt patient for information about exercise
Prompt patient for amount of sleep Confirm fasting by the patient Prompt patient to take morning bG measure By presenting the patient with a list of events, the patient begins to learn what factors may affect a particular measure. To construct a structured test, the patient may select which events are applicable to the patient. In a simplified embodiment, the selected events correlate directly to contextual criteria used to construct the test. Some of the events may be required for each sample instance (e.g., confirming amount of insulin taken or confirming fasting); whereas, other events may be optional (e.g., information about an evening snack or exercise).

Furthermore, the patient is presented with a prioritized list of contextual criteria. When constructing a structured test, the patient may select which of the contextual criterion (or contextual inputs) are applicable to the patient. For instance, a patient that typically enjoys an evening snack may choose to investigate the effect of their evening snack on the morning fasting value. The system would then present the user with a prioritized list of contextual criterion including the amount of their insulin administration, whether they consumed alcohol, the size of their snack, and the like. The user may then select the contextual criteria from the list that they would like to evaluate, and deselect those from the list that they would not. Collectively or individually, the contextual criterion can be thought of as a 'variable under test'. In other instances, a patient may select contextual criteria pertaining to exercising (such as the duration of exercise) but not snacking, or select contextual criteria pertaining to both snacking and exercising. Contextual criteria selected by the patient are captured by the diabetes manager at 57 and then used to construct at 58 a structured test for the patient in the manner further described below. It is readily understood that different types of measurements would correlate to different test templates and different test templates would be comprised of different events and/or contextual criteria. In other words, the selection of contextual criteria presented to the user may be a subset of contextual criteria which are filtered or pre-selected from a large grouping of criteria based upon the type of measurement.

In another example, the patient may select a TIPs test for a given event, such as a morning exercise regimen. For this type of measurement, the patient is requested to take a blood glucose measure before and after the given event. Depending of the selected event type, the patient is presented with a proposed test template for the selected event type. For a TIPs test associated with a morning exercise regimen, the proposed test template may include the following events:

Test template for morning exercise regimen:
Prompt patient for information about an evening snack
Confirm amount of insulin taken by the patient before sleeping
Prompt patient for amount of sleep
Prompt patient for information about breakfast
Confirm amount of insulin taken by the patient after breakfast
Prompt patient to take bG measure before exercise
Prompt patient to take bG measure after exercise
Prompt patient for information about the type and amount of exercise Typically, the patient is required to take the bG measures of a TIPs test within a window of time that encapsulates the given event (e.g., within an hour before and after exercising). To construct a structured test, the patient selects the contextual criterion applicable to the patient. It is noted that some of the contextual criterion may relate to different events, such as sleeping or breakfast, which can occur outside the window for taking the bG measures.

Alternatively, it may be more intuitive for the patient to begin by selecting an objective for the structured test as shown in FIG. 5B. For example, the patient may desire to know the effect of eating a snack or the effect of exercise on a particular measurement. In one embodiment, the patient may be presented at 53 with a plurality of different test objectives. The patient then selects an objective from the listing of different test objectives which is captured at 54 by the diabetes manager. The patient may also specify a particular measurement type. Given the test objective and/or measurement type input by the patient, the diabetes manager determines a proposed test template as indicated at 55. In an exemplary embodiment, each combination of test objective and measurement type maps to a proposed test template stored on the diabetes manager.

Two examples further illustrate how a selected test objective can be correlated to a proposed test template. In a first example, the patient may desire to understand the effect of eating an evening snack on a morning fasting measure. To understand the effect of the snack, each sample instance of the proposed test template may include the following events:

Test template A
Prompt patient to take a baseline bG measure prior to snack
Prompt patient for information about the snack
Prompt patient to take evening insulin
Confirm amount of insulin taken by the patient
Prompt patient for amount of sleep
Confirm fasting by the patient
Prompt patient to take morning bG measure Given test objective, the patient may be further presented with a prioritized list of contextual criteria related to snacking as described above.

In a second example, the patient may desire to understand the effect of exercising on a morning fasting measure. In this case, the test objective correlates to a different test template. Each sample instance of the proposed test template may include the following events:

Test template B
Prompt patient to take a baseline bG measure prior to exercising
Prompt patient for information about the exercise
Prompt patient to take evening insulin
Confirm amount of insulin taken by the patient
Prompt patient for amount of sleep
Confirm fasting by the patient
Prompt patient to take morning bG measure In this way, the proposed test template is related to the patient's selected test objective. Likewise, the patient may be presented with a prioritized list of contextual criteria related to exercising. When constructing a structured test, the patient may select which of the events and/or contextual criterion associated with the proposed test template are applicable to the patient. Contextual criteria selected by the patient are received at 57 and then used to construct 58 a structured test for the patient as further described below. It is envisioned that the selection of contextual criteria presented to the user may be a subset of contextual criteria which are filtered or pre-selected from a large grouping of criteria taking into account the identified objective.

Given a set of contextual criteria selected by the patient, the system may further prompt the patient for additional information related to the contextual criteria. For example, if the patient selected the contextual criteria for eating a snack, the system may prompt the patient to input a time or a window of time in which the patient eats the snack. The specified time is in turn used to schedule an appropriate reminder for the patient. For example, if the patient indicates their evening snack typically occurs between 8 pm and 9 pm, then the system could prompt the patient for information about the snack at 9:15 pm. In another example, the patient may indicate that the timing of their evening snack varies but they go to sleep at 11 pm. In this case, the system could prompt the patient for information about the snack just prior to 11 pm. If the patient fails to provide the requested information, the system may prompt the patient for the information at a later time (e.g., next morning prior to or at the time of bG measurement). It is readily understood that this scheduling approach could be extended to other types of contextual criteria. Alternatively, the patient may elect a less intrusive approach whereby contextual information is gathered from the patient at the time of the bG measurement. In any case, the system enables the patient to configure when and how the patient is to be prompted to input contextual information related to the bG measurement.

The structured test is constructed in accordance with the proposed test template, including the various contextual criteria and associated information specified by the patient. First, the structured test would include various mandatory events as specified by the proposed test. Continuing with the morning fasting measure set forth above, the structured test for the morning fast would include a prompting of the patient to take evening insulin, a query confirming the amount of insulin taken by the user, a query confirming the patient has been fasting, and a prompt of the patient to take morning bG measure. Each of these events would have an associated schedule.

In a simplified embodiment, the structured test would further include optional events selected by the patient. Each event may be associated with a pre-defined list of contextual criteria. Each criterion in turn corresponds to or is translated to one or more queries that are presented to the patient for purposes of collecting contextual data associated with the bG measurement. In another embodiment, the patient is present with a prioritized list of contextual criteria. Each contextual criterion selected by the patient from the list is then translated to one or more queries that are presented to the patient. In either embodiment, the corresponding queries become events in the structured test. Replies to the queries are captured by the system and stored with the corresponding bG measures. Each event and/or criterion would have a default schedule for the associated queries.

Continuing with the morning fasting measure, the patient may have selected events pertaining to an evening snack but not pertaining to exercising. In this case, the structured test would include one or more queries of the patient regarding their evening snack (e.g., what type of food was eaten, what was the portion size, how many carbohydrates were consumed, etc.). Furthermore, these queries would have an associated default schedule (e.g., immediately preceding prompt of patient to take morning bG measure). Given this exemplary scenario, the user specified structure test may be defined as follows:

Morning fast structure test

| Event | Schedule |
|---|---|
| Prompt patient to take evening insulin | March 6 at 10:00pm |
| Query insulin amount | March 6 at 10:00pm |
| Confirm fasting | March 7 at 8:00am |
| Prompt patient to take bG measure | March 7 at 8:00am |

-continued

| Event | Schedule |
|---|---|
| Query patient about evening snack | March 7 at 8:00am |

In this scenario, the patient specified a morning fasting measure to occur on March 7. Upon selecting the event for eating an evening snack, the patient may have further indicated the timing of their evening snack and/or bedtime, such that events are scheduled accordingly. It is envisioned that the timing of the events which comprise the structured test may also be configured directly by the patient or scheduled automatically by the system based upon information learned previously from the patient. The user defined structured test is stored by the diabetes manager for subsequent execution by the patient. Once a test has been defined by the patient, it can be selected and rerun multiple times at the patient's request.

In a more robust embodiment, the contextual criteria selected by the patient serve as adherence criteria for the structured test. Adherence criteria describe the conditions under which the structured test is administered to the patient. For a morning fasting measure, an exemplary adherence criterion is whether the patient has been fasting for at least 8 hours preceding the bG measure. Prior to taking a bG measure, the system may prompt the patient to confirm that they were fasting. With an affirmative reply from the patient, the adherence criterion is satisfied. Confirmation of fasting may be a required criterion for the morning fasting measure. When constructing the structured test, the patient may have also selected contextual criterion from the proposed test template. Likewise, the system will query the patient for contextual information associated with the selected criterion. The selected criterion can function as adherence criterion for the structured test. That is, sample data acquired under a given structured test will only be deemed acceptable when all of the adherence criteria for the given structured test are satisfied. In the context of the morning fasting measure, the patient may have selected contextual criterion pertaining to an evening snack. Thus, sample data from a given sample instance of the user-defined structured test will be deemed acceptable when the patient confirms fasting and provides information about their evening snack. If the patient fails to provide information about their evening snack, then the sample data from the sample instance is marked as unacceptable or discarded by the system.

Moreover, values associated with a selected contextual criterion may also serve as a second tier of adherence criteria. For example, confirming insulin taken may be a first tier adherence criterion for a given test. Prior to or at the time a test is first administered, the user may be prompted to input a particular amount of insulin taken. In reply, the user may specify 30 units of insulin were taken. In this example, the input value of 30 may serve as a secondary adherence criterion for this test. The user will be asked to confirm the quantity of insulin taken or queried to input the amount of insulin taken each time this test is administered going forward. If the user fails to confirm that 30 units of insulin were taken or inputs an amount different than 30, then the sample data from the sample instance may be marked as unacceptable for failure to meet this secondary adherence criteria since the context between the two sample instances vary.

Though both sample instances are valid, they should not be compared directly to each other without highlighting the differences. It is envisioned that contextual criteria may be designated in advance by system designers as being adherence criteria for the structured test or designated as such by the patient while defining the structured test. It is also envisioned that other types of testing criteria, such as entry criteria or exit criteria, can also be associated with a structured test. Further details regarding different types of testing criteria as well as how such criteria is implemented may be found in U.S. Patent Publication Nos. 2010/0212675 and 2010/0218132 which are incorporated by reference herein.

Figure 6:
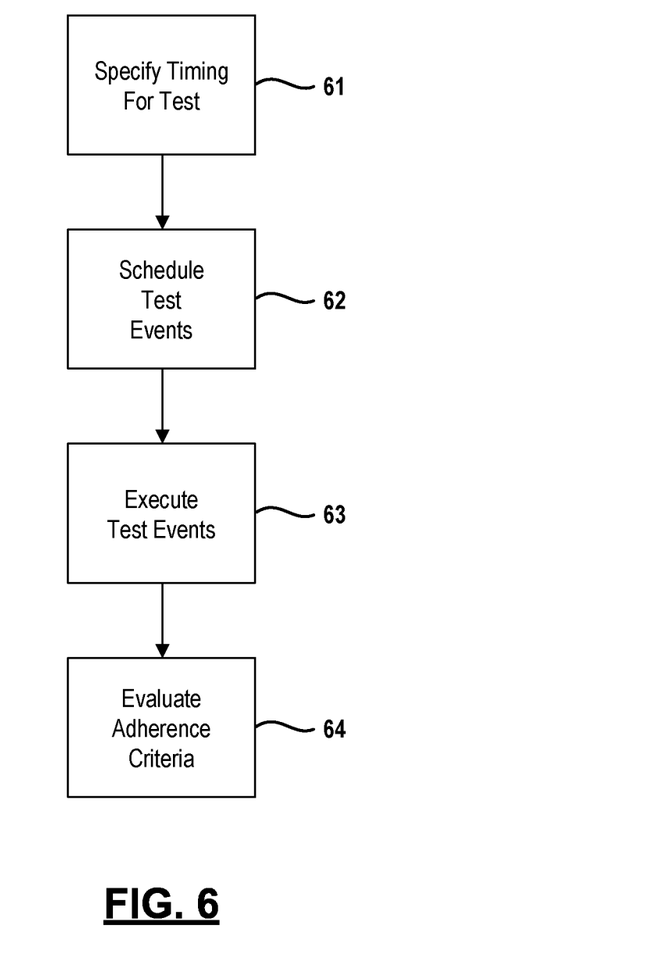
FIG. 6 is a flowchart depicting a method for implementing a structured test.

FIG. 6 depicts an exemplary method for implementing a structured test to the patient by the diabetes manager. A plurality of different structured tests, including those constructed by the patient in the manner set forth above, may be stored in the diabetes manager. A listing of available structured tests may be presented on a display for selection by the patient. Upon selecting a given structured test, the patient may specify at 61 the timing for execution of test. For example, a morning fast measure is to occur tomorrow morning. Based upon the specified timing for the test, each of the events associated with the structured test are scheduled at 62 by the diabetes manager. During execution of the test, the events are then executed at 63 in accordance with the event schedule. For each executed event, the diabetes manager collects and records data associated with the event. Data collected during the structured test is uniquely identified by test and/or event for subsequent reporting purposes.

After the test events have been executed, adherence criteria for the structured test are evaluated at 64. More specifically, each adherence criterion is evaluated by the diabetes manager. Sample data, including bG measures, acquired under the structured test are deemed to be acceptable when all of the adherence criteria for the structured test are satisfied. In this case, the sample data is retained for subsequent analysis and reported to either the patient or their healthcare provider. If one or more of the adherence criterion is not satisfied, then the sample data may be discarded or otherwise marked as being non-compliant with the test requirements. In other instances, the testing procedure may be discontinued when an adherence criterion is not met. For example, in a morning fast, the patient may not be prompted to provide a blood sample if they have not fasted a sufficient amount of time. When the structured test is comprised of single sample instance (i.e., one glucose measure or one TIPs test), then the structured test is complete. It is noteworthy that once a structure test has been constructed by the patient, the test may be executed repeatedly without modifications to its user specified parameters. That is, contextual criteria selected by the patient are carried forward when the test is executed in the future. It is understood that the diabetes manager may support modifications by the patient to a given structured test, such as adding or deleting contextual criterion. It is also understood that only the relevant steps of the methodology are discussed in relation to FIG. 6, but that other software-implemented instructions may be needed to control and manage the execution of a structure test by the system.

Structured tests, thus far, have been presented as being comprised of a single sample instance. Often times, test templates recommend or require acquiring multiple sample instances over a period of time. For instance, a test template may call for sample instances over a period of days, weeks or months to fully understand the effect of eating a snack on a morning fasting measure. These sample instances are collectively referred to as a sample group. For these types of structured test, adherence criteria defined for a sample instance is carried forward to each sample in the test. Adherence criteria can also be defined for a sample group and/or the overall test.

Moreover, when defining a test, the user can specify the reoccurrence frequency of the test. For example, the user can specify that a given test occur daily, weekly or at other reoccurring time intervals. User-defined contextual criteria will be carried forward to each sample instance of such reoccurring tests. In this way, multiple glucose measures acquired under similar context can be acquired, analyzed and reported to the user.

In another aspect of the disclosure, the patient may further specify the type of test. More specifically, the patient may be requested to categorize the type of test at the time the test is constructed or administered. Exemplary test types may include but are not limited to a 'typical', 'atypical' or 'delta' type of test. Each of these test types are further described below.

Given a scenario where a patient is trying to better understand the effect of a snack on their morning fasting measure, the system enables the patient to further categorize and thus compare sample data acquire in a given structured test or across similar structured tests. For example, assume that patient typically eats two scoops of ice cream each evening. During execution of a sample instance, the patient is prompted to further categorize the sample instance as being typical or atypical. Sample data acquired during the test can then be tagged accordingly. Given a sufficient number of sample instances, the system could provide the patient with information regarding the effect of this typical snack on their morning fasting measure (as compared, for example, to baseline measures where patient did not eat an evening snack). In the event that the patient has not established a baseline measure for the morning fast without having eaten an evening snack, the sample data for the typical snack is stored until a sufficient number of sample instances have been acquired to establish the baseline measure. The system could then retroactively analyze and report information regarding the effect of the typical snack on the morning fast measure.

Patients may vary from their typical snack from time to time. Variance may include but is not limited to the type of food, the quantity of food or the time at which the food was eaten. In this case, the patient may specify the sample instance as being 'atypical' when prompted to categorize the sample instance. The patient may be further prompted to label or describe the type of variance. Sample data acquired during the sample instance will be tagged accordingly. The system may disregard sample data tagged as 'atypical' when analyzing and reporting information regarding the effect of the typical snack on the morning fasting measure. Alternatively, the sample data tagged as 'atypical' may be compared with other atypical instances of similar construction. If a sufficient number of sample instances were acquired for a particular variant (e.g., ten instances when the patient ate pizza instead of ice cream or ate three scoops instead of two scoops of ice cream), the system could provide the patient with information regarding the effect of this particular atypical snack on their morning fasting measure.

In a 'delta' test, the patient would like to understand the effect of a change in their snack on their morning fasting measure. Accordingly, the system would guide the patient through a number of sample instances taken in a first (or before) context. After establishing a baseline measure, the system would prompt the patient to make a change in the variable under test, such as their evening snack. The system would then guide the patient through a series of additional sample instances taken in the changed (or after) context. Based on the collected sample data, the system could provide the patient with information regarding the effect of the change on their blood glucose measure.

Further scenarios are set forth which illustrate how these concepts are combined to provide a robust interface that enables patient to better understand factors affecting blood glucose measures. In a first scenario, a user would like to see the effect on their fasting of eating a large snack before bedtime. The user typically eats a small snack. To so do, the user selects a test objective (i.e., variable under test) as a 'morning fasting measure' with meal coupling. The user may further specify the test type as a 'delta' test type. To facilitate test setup, the system prompts the user for various inputs. For example, the system prompts the user for when fasting should be measured. The system prompts the user for when the meal intake will occur, with a default on the night before. The system may optionally prompts the user for the amount of carbs (range) that the small meal will entail as well as the amount of carbs (range) that the large snack will entail. The user then sets a start date for the test (default is immediate), and identifies when it should be run (e.g., weekdays, weekends, continuous, at request).

At the specified meal time, the system alerts the user to consume a small snack. As the system understands that this is a meal instance, it requests that the user input the amount of carbohydrates. If the user did not previously specify the anticipated range, the system utilizes the first value input by the user to establish a likely range (e.g., set at±fixed number of carbs from input value). The system may prompt the user to take their therapy (such as insulin or an oral antidiabetic agent) and confirms administration. The next morning, the system asks the user if they have been fasting since their nighttime snack. Upon confirmation of fasting, the system prompts the user to provide a blood sample and thus acquires a bG value. The system repeats this process at the specified time intervals until the variability associated with this action is established. Once variability has been established, the system will requests the new snack size, and repeats the process until the variability associated with the new snack size is established. Upon completion, the system generates and outputs a report to the user. In this way, the user can better understand the affect of their snack size on their blood glucose measures.

In a second scenario, a Type 1 diabetic user would like to see the effect of changing the timing on their pre-meal fast acting insulin dosage. The user thinks their 2 hr post prandial measure is too high. The user does not want to have the system evaluate the change, but wants to do it themselves. Therefore, the user defines a test to assess this scenario. In this case, the user selects the test objective as 'pre-post meal' and selects the test type as 'atypical' test. The system understands that the user is on insulin basal-bolus therapy. It prompts the user to identify which variable they are modifying (such as bolus amount, bolus timing, basal amount, meal size, pre-meal exercise). The user may select bolus timing, and the system asks for the offset the user is going to use. This becomes a tracking method for future review. If the user utilizes the conventional TIP approach, after the data is presented, it becomes useless (i.e., the user will not attribute the type of test to anything, therefore it has no value). In contrast, the system presented in this disclosure will support the historical review and comparison of similar tests.

During testing, the system first prompts the user to acquire their bG measure. The system then prompts the user to administer their insulin and confirms the insulin amount. The system may prompt the user to enter the meal size and prompts the user to begin eating. After eating, the system prompts the user to acquire the follow up bG value. If the user wants to compare results from two different sample groups, the system allows the user to select two stored sample groups having the same test parameters for review and comparison.

In a related scenario, the user may want to assess a range of pre-meal time of administration, ranging from 20 minutes before to 10 minutes after in 5 minute increments. In this case, the user will specify the test type as 'variable'. The user sets the start date (default is immediate), and identifies when it should be run (weekdays, weekends, continuous, at request), and which meals (breakfast, lunch, dinner, snack, all) the test applies to. The system then sequences the user starting from 0 to the extrema.

Figure 7:
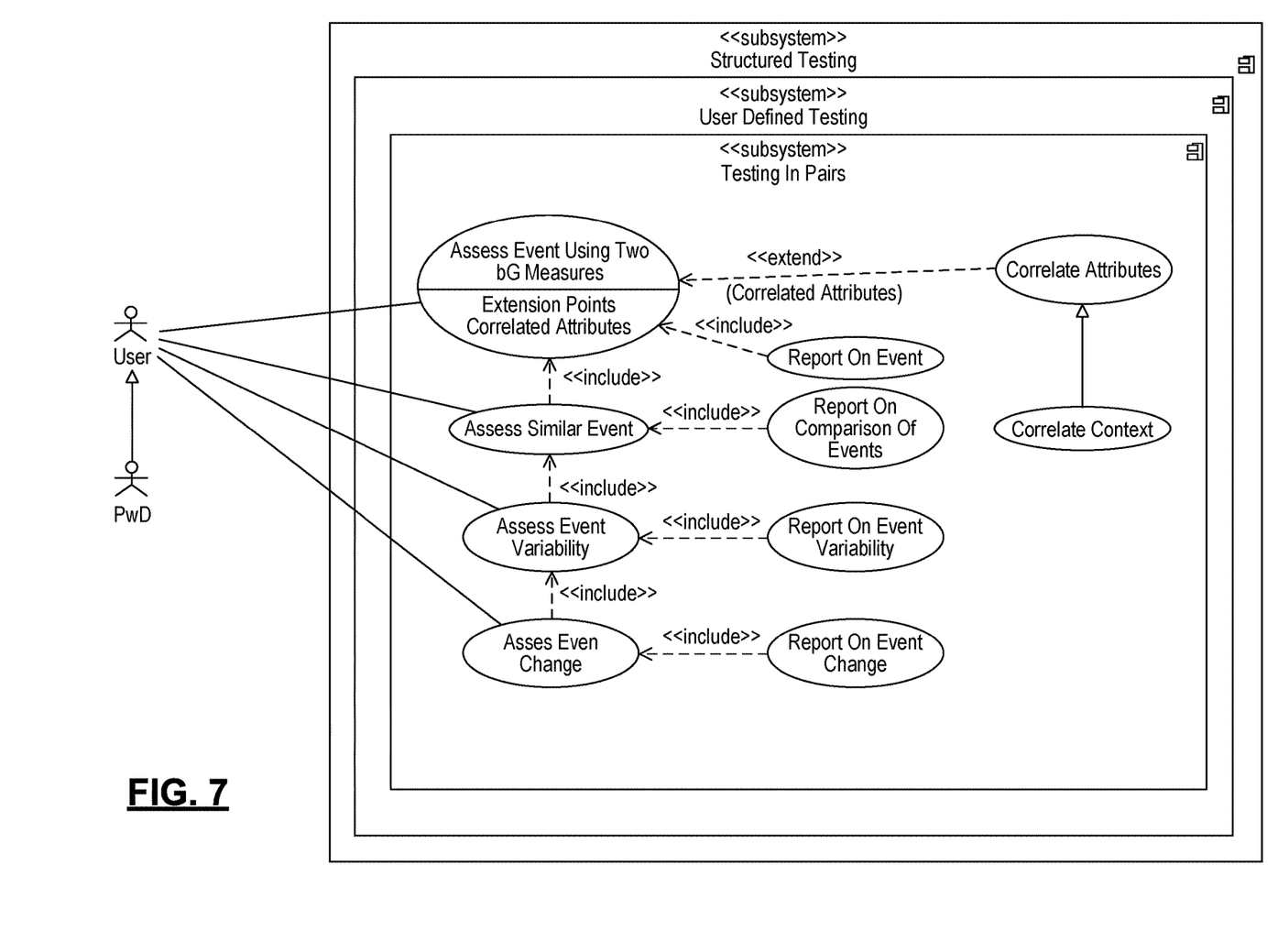
FIG. 7 is a diagram depicting exemplary use cases for report test results.

FIG. 7 illustrates exemplary use cases for reporting test results. Reporting use cases are described in the context of TIPs tests but are extendable to other types of structures tests. Note that contextual criteria are necessary to understand measures and are enforced by the system in the manner discussed above; whereas, attributes are information the user deems useful and provided at the discretion of the user. It is readily understood that the system may be configured to support such reporting use cases.

Reporting may be provided to compare events. For example, the system may provide or report a comparison of similar events. Events can be deemed similar when one or more contextual criteria for the acquired sample instance are the same. Other means for evaluating the similarity of events or the context under which sample instances were acquired are contemplated by this disclosure. Reporting on similar events can include highlighting similarities and/or difference in the testing context.

In other situations, events are expected to be different. This occurs when a TIP instance is re-run in atypical mode. In this case, the system highlights the differences in contexts, and shows the net effect on the variance of the resulting bG measure. For example, the user wants to ad-hoc evaluate the effect of eating a breakfast on their pre-lunch bG. They typically skip breakfast. The user creates a test in which they add the criterion of breakfast meal size to the lunch meal. The system shows two lunches. One with a breakfast meal size of 0, compared to a meal size of lets say 35 carbs. These values, as well as the resulting bG values are highlighted as compared to other attributes/contexts established across other similar TIP instances.

In another example, the user regularly eats breakfast, each with slightly different carb consumptions. The user has taken several TIP examples. The system shows the different similar TIP instances and highlights the different meal sizes and resulting bG values. Alternatively, the user regularly eats breakfast, each with slightly different carb consumptions. The user has taken different amounts of basal insulin across several TIP instances. The user wants to see the differences in the resulting bG measures. The system shows the user the similar tests, and highlights the differences in basal insulin amounts and meal size against the resulting bG measure.

Reporting may be provided on event variability. In this case, the user wants to evaluate the variability in bG based on an enforced similar event. The user is doing this so they can see how much base variability they have (or they regularly eat the same meal). In this case, the system will enforce the meal size consumed (second level adherence) and take multiple TIP instances for the purposes of assessing the variability as a statistical measure. For example, the user regularly eats a grilled chicken meal at lunch time, and wants to see the variability of their post meal value. The system prompts the user each lunch time to take the TIP value, and enforces the second level of adherence. In this case, the system does not report on the context, but on the variability, including the average bG measure, the range, and potentially other statistical measures (such as the median, max, min, and standard deviation). By using this example, the user will be 'self introduced' to meal coupling—the effect of the breakfast meal on the outcome of the lunch meal. Reporting on variability as applied to similar events or a sample group may also be extended and applied to multiple sample groups. Sample groups are first assessed for similarity and, if similar, further assessed for variability amongst the similar sample groups. The variability amongst sample groups may be then reported to the user.

Given the variability of a given sample group, the system can support additional functionality related to administering the associated structured test. For example, when variability is low (e.g., standard deviation is less than a pre-defined threshold), the user may be permitted to modify the event and/or contextual criteria (e.g., change the number of carbs consumed in a meal) because any change in bG will be attributable to the modification and not the variability in the sample group. When variability is high, the system may not permit the user to modify the event because any change may not be distinguishable from the sample instances and thus would not necessarily be attributable to the modification of the event. The system may further evaluate the amount of sample instances comprising the sample group and inform the user that more sample instances are needed to support accurate reporting. Other ways for re-configuring the protocol based on variability are also contemplated by this disclosure.

Reporting may also be provided on event change. In this case, the user has a regular event, and intends on changing the event. The user wants to see the effect of the change. For example, the user regularly runs 4 miles per day. The user wants to up their mileage to 5 miles per day, and wants to see the effect on the post run bG measure. For an ad-hoc evaluation, the user can merely compare two TIP instances. However, if the user wants more precision in their assessment, they can look at the variability. In this example, the system compares many prior runs at 4 miles (either retrospectively because they exist, or perspectively, by asking the user to run a predetermined number of runs at 4 miles). The system then prompts for the increase in mileage. The resulting report shows a statistical comparison to the two different runs including the change in mean/median, whether the change was real (t-test or equivalent), and the like. It is readily understood that other reporting use case may be developed and supported by the system.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A method for collecting biomarkers from a patient, comprising:

presenting, by a diabetes management device, the patient with a plurality of contextual criterion for a structured test, where the structured test comprises of a series of steps to be performed by the patient to evaluate an effect of one or more contextual criterion on the biomarkers of the patient;

receiving, by the diabetes management device, selection of one or more contextual criterion by the patient from the plurality of contextual criterion, where the receipt of the selection of the one or more contextual criterion is in response to presenting the patient with the plurality of contextual criterion;

constructing, by the diabetes management device, the structured test using a test template that specifies one or more collection events for collecting the biomarkers and using the contextual criterion selected by the patient, where the construction of the structured test is in response to receiving the selection of the one or more contextual criterion;

administering, by the diabetes management device, the structured test to the patient, where the administration of the structured test includes prompting the patient with prompts to perform the series of steps over a period of time, receiving replies from the patient in response to prompting the patient with the prompts, and where at least one step in the series of steps is measuring biomarker data from the patient using a collection device;

evaluating, by the diabetes management device, whether a given contextual criterion selected by the patient has been met during the administration of the structured test; and tagging, by the diabetes management device, the biomarker data measured during the structured test by the collection device as non-compliant when the given contextual criterion was not met during the administration of the structured test.

2. The method of claim 1 further comprises reporting the biomarker data measured during the structured test as compliant when the given contextual criterion selected by the patient was met during the administration of the structured test.

3. The method of claim 1 wherein administering the structured test further comprises querying the patient for each contextual input, receiving replies to the queries from the patient and associating the replies to the queries with the biomarker data measured during the structured test.

4. The method of claim 1 wherein:
a first one of the series of steps is providing a first sample of blood into the collection device before a test event,
a second one of the series of steps is providing a second sample of blood into the collection device after the test event, where the first and second ones of the series of steps are within a window of time that encapsulates the test event, and
administering the structured test further comprises querying the patient for contextual data regarding a second test event that differs from the test event.

5. The method of claim 4 wherein administering the structured test further comprises querying the patient for contextual data regarding a third test event that occurs outside the window of time.

6. The method of claim 4 wherein at least one step in the series of steps is inputting a third sample of blood into the collection device at a time that occurs outside of the window of time.

7. A method for collecting blood glucose measures from a patient, comprising:
presenting, by a diabetes management device, the patient with a plurality of contextual criterion for a structured test, where the structured test comprises of a series of steps to be performed by the patient to evaluate an effect of one or more contextual criterion on the blood glucose measures of the patient;
receiving, by the diabetes management device, selection of one or more contextual criterion by the patient from the plurality of contextual criterion where the receipt of the selection of the one or more contextual criterion is in response to presenting the patient with the plurality of contextual criterion;
constructing, by the diabetes management device, the structured test using a test template that specifies one or more collection events for collecting the blood glucose measures and using the contextual criterion selected by the patient, where the construction of the structured test is in response to receiving the selection of the one or more contextual criterion;
administering, by the diabetes management device, the structured test to the patient multiple times over a period of time, thereby acquiring one or more sample instances for each structured test in a series of administered structured tests, where administering the structured test includes prompting the patient with prompts to perform the series of steps, receiving replies from the patient in response to prompting the patient with the prompts, and where at least one step in the series of steps is measuring a blood glucose level of a sample of blood using a glucose meter, a first step in the series of steps is providing a first sample of blood to the glucose meter before a test event and a second step in the series of steps is providing a second sample of blood after the test event;
evaluating, by the diabetes management device, whether a given contextual criterion selected by the patient has been met during the administration of a given structured test; and
tagging, by the diabetes management device, sample instances acquired during the given structured test as non-compliant or discarding the sample instances when the given contextual criterion was not met during the administration of the given structured test.

8. The method of claim 7 further comprises reporting the sample instances acquired during the structured test as compliant when the given contextual criterion selected by the patient was met during the administration of the given structured test.

9. The method of claim 7 wherein administering the structured test further comprises querying the patient for the one or more contextual criterion, receiving replies to the queries from the patient and associating the replies to the queries with data collected during the structured test.

10. The method of claim 7 wherein administering the structured test further comprises querying the patient for contextual data regarding a second test event that occurs outside a window of time.

11. The method of claim 7 further comprises analyzing the sample instances acquired over the series of the structured tests and presenting results from the analysis to the patient.

12. The method of claim 11 wherein:
at least one step in the series of steps is categorizing the sample instance for the given structure test, and
administering the structured test includes disregarding the sample instance for the given structured test from subsequent analysis when the sample instance is categorized by the patient as atypical.

13. The method of claim 11 wherein:
administering the structured test comprises querying the patient for at least one contextual criterion during administration of a given structured test, and receiving a reply to the query from the patient,
at least one step in the series of steps is categorizing the sample instance for the given structured test, and
administering the structured test comprises disregarding the sample instance for the given structured test from subsequent analysis when the sample instance is categorized as atypical by the patient.

14. The method of claim 7 further comprises
guiding the patient through a first series of structured tests constructed using the contextual criteria selected by the patient;
deriving a baseline blood glucose measure from the sample instances acquired during the first series of structured tests;
prompting the patient to change a variable associated with the first series of structured tests;
guiding the patient through a second series of structured tests, where the second series of structured tests have a value for the variable different from the first series of structured tests but otherwise constructed using the contextual criteria selected by the patient; and
deriving a changed blood glucose measure from the sample instances acquired during the second series of structured tests.

15. The method of claim 14 further comprises presenting results from the first and second series of structured tests to the patient, including a comparison of the baseline blood glucose measure and the changed blood glucose measure.

16. The method of claim 14 further comprises analyzing the sample instances acquired during the first and second series of structured tests and presenting results from the analysis to the patient.

17. A method for collecting blood glucose measures from a patient, comprising:

presenting, by a diabetes management device, the patient with a plurality of contextual criterion for a structured test;

receiving, by the diabetes management device, selection of one or more contextual criterion by the patient from the plurality of contextual criterion, where the receipt of the selection of the one or more contextual criterion is in response to presenting the patient with the plurality of contextual criterion;

constructing, by the diabetes management device, the structured test using the contextual criterion selected by the patient, where the construction of the structured test is in response to receiving the selection of the one or more contextual criterion and where the structured test comprises of a series of steps to be performed by the patient to evaluate an effect of the one or more contextual criterion on the blood glucose measures of the patient;

administering, by the diabetes management devices, the structured test, where the administration of the structured test includes:

prompting, by the diabetes management device, the patient with prompts to perform the series of steps, where at least one step in the series of steps is inputting a blood sample into the diabetes management device;

receiving, by the diabetes management device, replies from the patient in response to prompting the patient with the prompts;

measuring, by the diabetes management device, a blood glucose level using the blood sample;

evaluating, by the diabetes management device, whether a given contextual criterion selected by the patient has been met during the administration of the structured test; and tagging, by the diabetes management device, the blood glucose level measured during the structured test as non-compliant when the given contextual criterion was not met during the administration of the structured test.

18. The method of claim 17, wherein the plurality of contextual criterion includes at least one of a snack, exercise, and sleep.

* * * * *